United States Patent [19]

Pfeifer

[11] Patent Number: 6,107,097
[45] Date of Patent: Aug. 22, 2000

[54] SYNTHETIC TEST SOIL

[75] Inventor: Martin Pfeifer, Waldkraiburg, Germany

[73] Assignee: Pereg GmbH, Germany

[21] Appl. No.: 09/117,228

[22] PCT Filed: Jan. 24, 1997

[86] PCT No.: PCT/EP97/00337

§ 371 Date: Jul. 24, 1998

§ 102(e) Date: Jul. 24, 1998

[87] PCT Pub. No.: WO97/27482

PCT Pub. Date: Jul. 31, 1997

[30] Foreign Application Priority Data

Jan. 25, 1996 [DE] Germany ............ 196 02 673

[51] Int. Cl.[7] .......... G01N 33/86; G01N 33/72; C12Q 1/56; A61K 35/14
[52] U.S. Cl. ............ 436/69; 436/66; 435/13; 435/214; 530/381; 530/382; 530/385
[58] Field of Search .......... 530/381, 382, 530/385; 435/214, 13; 436/66, 69

[56] References Cited

U.S. PATENT DOCUMENTS 5,476,771  12/1995  Reid et al. ............... 435/13
5,508,202   4/1996  Enomoto et al. .......... 436/69

FOREIGN PATENT DOCUMENTS 480843      4/1992  European Pat. Off. .
WO 92/22312 12/1992  WIPO .

OTHER PUBLICATIONS

Tzvetanova and Gotzev, "Improved Biuret Method for Determination of Fibrinogen," *Clin. Chem.* 34: 430–431 (1988).

*Primary Examiner*—Karen Cochrane Carlson
*Assistant Examiner*—Holly Schnizer
*Attorney, Agent, or Firm*—Medlen & Carroll, LLP

[57] ABSTRACT

The present invention provides methods and compositions relating to synthetic test stains comprising isolated fibrin and/or fibrin precursors and blood plasma proteins. Kits for the preparation of synthetic test stains containing an isolated fibrin precursor and an initiator for converting the fibrin precursor to fibrin are also provided. In addition, methods for checking the efficiency of cleaning processes, and kits for carrying out these methods are provided.

14 Claims, No Drawings

SYNTHETIC TEST SOIL

This application claims priority to PCT Application No. PCT/EP97/00337, Jan. 24, 1997, which claims foreign priority to German Application No. 196 02 673.3, filed Jan. 25, 1996.

FIELD OF THE INVENTION

The invention relates to a synthetic test stain, to the use of a fibrin glue for the preparation of said stain, to a kit for the preparation of a synthetic test stain, to a method of checking the efficiency of a cleaning process, and to a kit for carrying out this method.

BACKGROUND OF THE INVENTION

Many medical and surgical instruments and apparatuses must be cleaned, disinfected and sterilized after use. Cleaning and disinfection are conventionally carried out in so-called automatic washing/disinfecting machines. In these machines the instruments are cleaned, disinfected and dried in preparation for subsequent sterilization.

It is a requirement of the German Law of Medical Products, and comparable regulations in other countries, that the mechanical cleaning process used should be checked for efficiency. On the one hand, this embraces a homologation of the process, which the manufacturer of the automatic washing/disinfecting machine has to undertake before it can be marketed. On the other hand, the user must check the cleaning power of the machine at regular intervals.

To check the cleaning power, so-called test samples with defined test stains are required. The most stubborn stain on medical and surgical instruments and apparatuses, and the one which is hardest to remove, is normally coagulated blood.

In the prior art the homologation to be undertaken by the manufacturer is therefore often carried out with fresh human blood as the test stain. Fresh blood is required because stored blood has had its coagulation reduced by the addition of anticoagulants. However, it is not practicable for the user to employ fresh human blood for regular checking of the cleaning power.

The prior art (established prior use) therefore proposes a variety of test stains such as semolina, egg yolk, starch or stains containing flour. As the properties of all these test stains are markedly different from those of blood, the evidence obtainable on the efficiency of the cleaning process in respect of bloodstains is nonexistent or at best imprecise.

SUMMARY OF THE INVENTION

The present invention provides synthetic test stain comprising a first component selected from the group consisting of fibrin and fibrin precursor, and a combination thereof, and a second component, wherein said second component comprises hemoglobin. In some embodiments, the fibrin precursor is fibrinogen. In other embodiments, the fibrin is selected from the group consisting of monomeric fibrin, polymeric fibrin and crosslinked fibrin. In 'still other embodiments, the synthetic test stain further comprises at least one blood plasma protein. In some preferred embodiments, the blood plasma protein is albumin or a combination of albumin and hemoglobin. In still other embodiments, the synthetic test stain further comprises fibrin glue. In particularly preferred embodiments, the fibrin glue comprises fibrinogen and thrombin.

The present invention also provides kits for the preparation of synthetic test stains, comprising at least one fibrin precursor and an initiator for converting said fibrin precursor to fibrin. In some preferred embodiments, the fibrin precursor comprises fibrinogen. In still other embodiments, the fibrin precursor comprises at least one blood clotting factor. In particularly preferred embodiments, the blood clotting factor is selected from the group consisting of $Ca^{2+}$ ions and clotting factor XIII. In yet additional embodiments, the initiator comprises thrombin. In further embodiments, the fibrin precursor and said initiator are lyophilized. In still other embodiments, the kits further comprise at least one solvent, and/or at least one blood plasma protein, and/or at least one fibrinolytic agent, and/or at least one antifibrinolytic agent. In some embodiments, the fibrinolytic agent is plasminogen. In other embodiments, the antifibrinolytic is aprotinin. In particularly preferred embodiments, both the fibrin precursor and the initiator are provided in isotonic solutions.

The present invention also provides methods for determining the efficiency of a cleaning process, comprising the steps of: providing a synthetic test stain comprising at least one component selected from the group consisting of fibrin and fibrin precursors, and a sample; applying said synthetic test stain to said sample to create a test sample; subjected said test sample to a cleaning process; and detecting the presence of said test stain on said test sample. In some embodiments, the method further comprises the steps of coagulating and drying said test stain after applying said synthetic test stain to said sample. In some preferred embodiments, the detecting step comprises observing a chemical color reaction. In particularly preferred embodiments, the color reaction is the biuret reaction.

The present invention also provides kits for determining the efficiency of a cleaning process, wherein said kit comprises a test sample having a synthetic test stain and at least one analytical reagent suitable for detecting residues of said test stain in said test sample. In some embodiments, the analytical reagents comprise an alkaline aqueous solution and an aqueous solution of $Cu^{2+}$ ions. In still other embodiments, the alkaline aqueous solution comprises a complexing agent for $Cu^{2+}$ ions.

The object of the invention is to provide a synthetic test stain which is easy to handle and which, as regards its removability in a cleaning process, behaves more like fresh human blood than do the test stains of the prior art.

The invention achieves this object through the fact that the synthetic test stain contains fibrin and/or a fibrin precursor. Within the framework of the invention, the term "fibrin" is understood to include both monomeric and polymeric fibrin and/or crosslinked fibrin.

Within the framework of the invention, the term "synthetic test stain" includes any test stain in which fibrin and/or the fibrin precursor has been added separately (e.g. in isolated form and not as a constituent of native human or animal blood). Thus the term does not include test stains in which fresh or coagulated native blood is mixed with other constituents, none of which contains any fibrin or any fibrin precursor.

DESCRIPTION OF THE INVENTION

The invention has recognized that the difficult removability of a fresh bloodstain is due primarily to blood coagulation (conversion of fibrinogen to fibrin and possible subsequent crosslinking) and that a test stain containing fibrin or fibrin precursors has very similar properties in respect of removability. This is surprising insofar as the clotting factors account for only a very small proportion of the blood components. This can be illustrated with an example. One liter of human blood contains about 520 ml of blood plasma, this plasma contains about 35 g of plasma proteins and these in turn contain only a very small proportion of fibrinogen as the fibrin precursor. The surprising discovery of the invention is that the behaviour of blood in a cleaning process can be simulated well by a synthetic test stain which contains fibrin and/or a fibrin precursor, even though fibrinogen/fibrin only accounts for a proportion of less than 0.5% of the blood components.

The fibrin precursor is preferably fibrinogen. The test stain according to the invention can contain additional blood plasma proteins, e.g. albumin and/or haemoglobin, in order to simulate the properties of blood even better. The invention thus provides a synthetic test stain which, as far as cleaning technology is concerned, behaves like native blood to a good approximation, although it does not consist of native blood itself but is prepared synthetically from various blood constituents which essentially determine the staining properties of blood.

The invention also provides the use of a fibrin glue for the preparation of a synthetic test stain according to the invention. Commercially available fibrin glues are two-component or multicomponent systems, one component containing fibrinogen as the fibrin precursor and the other component containing thrombin. Thrombin is a proteolytic enzyme and one of the blood clotting factors, effecting the conversion of fibrinogen to fibrin. Normally a fibrin glue also contains blood clotting factor XIII, which initiates the crosslinking of fibrin to fibrin polymers. Other conventional constituents are $Ca^{2+}$ ions (blood clotting factor IV) as activators of the enzymatic systems active in blood clotting, and fibrinolytics (e.g. plasmin or its precursor plasminogen) and/or antifibrinolytics (e.g. aprotinin).

One fibrin glue kit which can be used within the framework of the invention is e.g. TISSUCOL® from Immuno GmbH, 69126 Heidelberg.

The invention also provides a kit for the preparation of a synthetic test stain, said kit having the following components:
a) a fibrin precursor,
b) a conversion initiator for the fibrin precursor.

The term "conversion initiator" includes any substances which initiate and/or promote the conversion of the fibrin precursor to monomeric fibrin and/or the polymerization or crosslinking of fibrin.

It is pointed out that the list of these components does not have to imply a limitation: the kit can also contain more than two components. Thus e.g. the fibrin precursor and the conversion initiator can be present as solids in lyophilized form, which first have to be dissolved with suitable solvents. These solvents can then also be part of the kit.

Component a) preferably contains fibrinogen and component b) preferably contains thrombin. Component a) can additionally contain other blood plasma proteins, e.g. albumin and/or haemoglobin.

It is frequently appropriate for component a) to contain blood clotting factor XIII, which has a crosslinking action on fibrin and thereby enhances coagulation. This produces a stubborn test stain which is particularly difficult to remove. It is also preferable if one of the components of the kit contains $Ca^{2+}$ ions (blood clotting factor IV). Finally, the kit can optionally contain other substances, e.g. fibrinolytics such as plasminogen or antifibrinolytics such as aprotinin.

The components of the kit can be present e.g. as a solution in isotonic saline. Alternatively, as already stated above, they can be present as solids (lyophilized), in which case suitable solvents are also part of the kit.

A further aspect of the invention is a method of checking the efficiency of a cleaning process. It comprises the following steps:
a) applying a synthetic test stain according to one of claims 1 to 4 to a test sample,
b) subjecting the test sample to the cleaning process to be tested,
c) detecting residues of the test stain on the test sample.

As far as material and surface structure are concerned, the test samples should be as closely equivalent as possible to the instruments and apparatuses to be cleaned in practice. To simulate the cleaning of surgical instruments, it is possible to use e.g. 1 to 2 mm thick stainless steel plates with dimensions of 100×20 mm. Various surface contours, such as ribs, bosses etc., can be provided in order to simulate corresponding "dirty corners" of surgical instruments. The surface of the test samples can be roughened (e.g. with abrasive grain 180 (abraded surface according to DIN 17440 IV, grain 180)) in order to improve the adhesion of the test stain and thereby ensure that the test sample is more likely to be harder to clean than instruments and apparatuses used in practice. It is also conceivable to use stainless steel screws as test samples because the screw head and thread have regions of their surface which are comparatively difficult to clean.

In order to check the cleaning action in the case of endoscopes, it is possible to use test samples with internal cavities or plastic or rubber tubes with narrow lumina. At least part of the internal spaces or tube lumina should be visible from the outside (e.g. by using transparent tube material) so as to allow the detection of residues of the test stain on this surface, said detection preferably including an optical examination. The synthetic test stain can be applied e.g. by spraying of the components of a kit according to one of claims 6 to 11 or by some other method of application. The application step can preferably be followed by a step in which the test stain is left to coagulate and/or dried. Coagulation can also take place during drying, in which case a separate coagulation step is unnecessary. It will often be preferable, however, to allow the test stain time to coagulate before drying. For this purpose the test sample can be exposed e.g. for ca. 10 min at 20° C. to an environment with a relative humidity of 90%. Within the framework of the invention, the term "coagulation" includes the conversion of any fibrin precursors present (fibrinogen) to fibrin. Coagulation preferably also includes polymerization of the fibrin monomers to a fibrin network, preferably under the action of blood clotting factor XIII and $Ca^{2+}$ as a cofactor (blood clotting factor IV). Said polymerized and crosslinked fibrin network is a particularly good simulation of the conditions present in the case of coagulated bloodstains on medical instruments.

The test stain can be dried at room temperature; suitable periods can be e.g. between 1 and 24 h. Drying at elevated temperature (e.g. 40° C.) for e.g. 1 h is a further possibility. A particularly stubborn test stain can be created when the test stain according to the invention, which may have been coagulated and dried, is additionally treated with disinfectants and hence partially denatured. Denatured blood residues are particularly difficult to remove and arise in practice when e.g. surgical instruments are stored in containers with disinfectant solution, either immediately after use or sometime later.

This preparation of the test sample can be carried out by the user; alternatively, however, as explained below, it is possible to provide test kits which contain appropriately prepared test samples.

The test sample or samples treated with the test stain are then subjected to the cleaning process to be tested. When cleaning is complete, the test sample is examined for any residues of the test stain.

The preferred procedure, and the simplest for the user, is a visual detection of any residues, preferably after a colour reaction has been carried out to stain protein residues present on the test sample. A conventional reaction for the detection of proteins, which is familiar to those skilled in the art, is e.g. the biuret reaction. The following non-limiting list contains further examples of possible detection reactions:

Kjeldahl reaction, Lowry reaction, Millon reaction, ninhydrin reaction, Pauly reaction, xanthoprotein reaction.

A separate protein colour reaction may be unnecessary if the test stain according to the invention contains haemoglobin, which considerably facilitates optical recognition of the residual stain.

A somewhat more expensive possibility is to hydrolyse the proteins still adhering to the test sample, and analyse the amino acids which result as hydrolysis products.

If a quantitative detection is required, the proteins of the test stain preferably contain radioactive tracers such as $^{99m}$Tc. The cleaning action can then be assessed by measuring the $^{99m}$Tc γ radiation emanating from the test sample before and after cleaning. This procedure also makes it possible to calibrate the synthetic test stain according to the invention or the test method according to the invention, because comparative measurements can be carried out with native blood which is also labelled with $^{99m}$Tc. The composition of the test stain according to the invention can be varied so that its behaviour towards cleaning can be made as closely equivalent as possible to the behaviour of native blood.

The invention also provides a kit for carrying out the method according to the invention, which contains the following parts:

a test sample provided with a synthetic test stain, analytical reagents for detecting residues of the test stain.

This kit provides every user with a simple routine means of checking the efficiency of his automatic washing/disinfecting machine. The preprepared test sample or samples are taken out of the kit and subjected to the cleaning process to be tested. The analytical reagents contained in the kit are then used in the manner described above to detect and visually assess residues of the test stain.

The biuret reaction is preferably used as the detection reaction. In this case the analytical reagents contain on the one hand an alkaline aqueous solution and on the other hand an aqueous solution of $Cu^{2+}$ ions. The alkaline aqueous solution preferably additionally contains a complexing agent for $Cu^{2+}$ ions in order to prevent copper(II) hydroxide from precipitating in the alkaline medium. Nitrilotriacetic acid (NTA) or its salts, for example, can be used as suitable complexing agents. Other known complexing agents for $Cu^{2+}$ ions (EDTA etc.), which are familiar to those skilled in the art, are also suitable.

Examples of the invention are described below. All percentages are by weight.

EXPERIMENTAL

Example 1

This Example describes the preparation of components of a kit for the preparation of a synthetic test stain according to the invention.

Component a):

0.4 g of fibrinogen and 200 U of blood clotting factor XIII are dissolved in 50 ml of isotonic (0.9%) saline. One unit, U, of blood clotting factor XIII corresponds to the activity contained in 1 ml of fresh normal plasma.

Component b):

2500 IU of thrombin (human), 8 g of albumin and 30 mg of $CaCl_2.2H_2O$ are dissolved in 50 ml of isotonic saline. One international unit (IU) of thrombin is defined as the activity contained in 0.0853 mg of the 1st international standard of human thrombin.

Based on the total amount of liquid in the two components (100 ml), the proportion of fibrinogen is 0.4% by weight and the proportion of albumin is 8% by weight. These proportions can be varied (e.g. in the range 0.1 to 0.5% by weight or 5 to 10% by weight, respectively) in order to vary the "stubbornness" of the test stain to be prepared from the components.

The ingredients of components a) and b) are obtainable as parts of a fibrin glue kit, e.g. the TISSUCOL® kit from Immuno GmbH which has already been mentioned above.

The kit prepared according to this Example contains blood clotting factor XIII and calcium chloride as a cofactor in order to promote the crosslinking of fibrin to a polymeric network and thereby produce a stubborn stain. If a particularly stubborn test stain is desired, components a) and b) can also be more highly concentrated; for example, said amounts of protein and auxiliary can each be dissolved in only 5 ml of isotonic saline.

Example 2

This Example describes the preparation of components of a second kit for the preparation of a synthetic test stain according to the invention.

Component a):

0.4 g of fibrinogen is dissolved in 50 ml of isotonic (0.9%) saline.

Component b):

25 IU of thrombin (human), 8 g of albumin, 8 g of haemoglobin and 30 mg of $CaCl_2.2H_2O$ are dissolved in 50 ml of isotonic saline.

Based on the total amount of liquid in the two components (100 ml), the proportion of fibrinogen is 0.4% by weight and the proportion of albumin and haemoglobin is 8% by weight. These proportions can be varied (e.g. in the range 0.1 to 0.5% by weight or 5 to 10% by weight, respectively) in order to vary the "stubbornness" of the test stain to be prepared from the components.

In this kit the proportion of thrombin in component b) has been markedly reduced in order to prevent coagulation from occurring during the application of the test stain. The haemoglobin allows a visual assessment of any residues of the test stain to be made without the need to perform a separate colour reaction for visualization.

Example 3

Preparation of the components of an analytical reagent

Solution 1: 3 g of NaOH and 4 g of NTA (nitrilotriacetic acid) are dissolved in 50 ml of water.

Solution 2: 5 g of $CuSO_4.5H_2O$ are dissolved in 50 ml of water.

These two solutions together give the analytical reagent for the biuret reaction.

Example 4

Application of the test stain to a test sample

A 2 mm thick stainless steel plate with dimensions of 100 ×20 mm is used as the test sample. The surface of the plate is an abraded surface according to DIN 17440 IV, grain 180.

The surface of the test sample is wetted with equal proportions by volume of components a) and b) from Example 1. For example, the two components a) and b) can be sprayed simultaneously onto the test sample surface to be wetted, or applied in some other way.

The test stain is then left to coagulate for 10 min at room temperature (20° C.) and 90% relative humidity. Coagulation includes the conversion of fibrinogen to fibrin and the crosslinking of the fibrin monomers to a polymeric network. After coagulation, the test sample is dried at 40° C. for 1 h in a drying cabinet. After drying, the test sample is ready to use. It can be dispatched to a user, optionally together with an analytical reagent according to Example 3.

Example 5

Implementation of the method according to the invention
The test sample according to Example 4 is placed in the automatic washing/disinfecting machine to be tested and is subjected to a conventional cleaning cycle.

Equal amounts of solutions 1 and 2 from Example 3 are mixed together to form an analytical reagent, in which the cleaned test sample is immersed. The residence time of the test sample in the analytical reagent is preferably at least 60 s. If protein residues are still present on the test sample, the peptide bonds and (if present) tyrosine residues complex the $Cu^{2+}$ ions to give a purple-coloured complex, so residues of the test stain on the test sample surface are recognizable by a purple colouration. With this detection method protein residues can still be recognized visually down to a limit of about 1 to 4 $\mu g/cm^2$ on the metal surface.

What is claimed is:

1. A synthetic test stain comprising:
   a) a first component selected from the group consisting of fibrin and fibrin precursor, and a combination thereof, and
   b) a second component, wherein said second component comprises hemoglobin.

2. The synthetic test stain of claim 1, wherein said fibrin precursor is fibrinogen.

3. The synthetic test stain of claim 1, wherein said fibrin is selected from the group consisting of monomeric fibrin, polymeric fibrin and crosslinked fibrin.

4. The synthetic test stain of claim 1, further comprising at least one blood plasma protein.

5. The synthetic test stain of claim 4, wherein said blood plasma protein is albumin.

6. The synthetic test stain of claim 1, further comprising fibrin glue.

7. The synthetic test stain of claim 6, wherein said fibrin glue comprises fibrinogen and thrombin.

8. A method for checking the efficiency of a cleaning process, comprising the steps of:
   a) providing: i) a synthetic test stain comprising at least one component selected from the group consisting of fibrin and fibrin precursors, and
   ii) a sample;
   b) applying said synthetic test stain to said sample to create a test sample;
   c) subjected said test sample to a cleaning process; and
   d) detecting the presence of said test stain on said test sample.

9. The method of claim 8, further comprising the steps of coagulating and drying said synthetic test stain after applying said synthetic test stain to said sample in step b).

10. The method of claim 8, wherein said detecting comprises observing a chemical color reaction.

11. The method of claim 10, wherein said color reaction is the biuret reaction.

12. A kit for checking the efficiency of a cleaning process, wherein said kit comprises a test sample having a synthetic test stain and at least one analytical reagent suitable for detecting residues of said test stain in said test sample.

13. The kit of claim 12, wherein said analytical reagents comprise an alkaline aqueous solution and an aqueous solution of $Cu^{2+}$ ions.

14. The kit of claim 13, wherein said alkaline aqueous solution comprises a complexing agent for $Cu^{2+}$ ions.

* * * * *